United States Patent
Pedersen

(10) Patent No.: US 10,645,953 B2
(45) Date of Patent: May 12, 2020

(54) **USE OF ZINC AND COPPER GLUCONATE IN THE TREATMENT OF METHICILLIN-RESISTANT *STAPHYLOCOCCUS AUREUS***

(71) Applicant: Jens Jorgen Pedersen, Tars (DK)

(72) Inventor: Jens Jorgen Pedersen, Tars (DK)

(73) Assignees: DANTRACE-DANFEED IVS, Taars (DK); Distributors Processing, Inc., Porterville, CA (US)

( * ) Notice: Subject to any disclaimer, the term of this patent is extended or adjusted under 35 U.S.C. 154(b) by 58 days.

(21) Appl. No.: 15/557,068

(22) PCT Filed: Mar. 11, 2016

(86) PCT No.: PCT/DK2016/050069
§ 371 (c)(1),
(2) Date: Sep. 8, 2017

(87) PCT Pub. No.: WO2016/141946
PCT Pub. Date: Sep. 15, 2016

(65) Prior Publication Data
US 2019/0110499 A1     Apr. 18, 2019

(30) Foreign Application Priority Data
Mar. 11, 2015  (DK) ................................ 2015 00152

(51) Int. Cl.
| | | |
|---|---|---|
| *A23K 20/20* | (2016.01) | |
| *A23K 20/105* | (2016.01) | |
| *A23K 50/30* | (2016.01) | |
| *A61K 33/30* | (2006.01) | |
| *A61K 33/34* | (2006.01) | |
| *A61K 9/00* | (2006.01) | |
| *A61P 31/04* | (2006.01) | |
| *A61K 33/32* | (2006.01) | |
| *A61K 9/14* | (2006.01) | |
| *A61K 9/20* | (2006.01) | |

(52) U.S. Cl.
CPC ............ *A23K 20/30* (2016.05); *A23K 20/105* (2016.05); *A23K 50/30* (2016.05); *A61K 9/0053* (2013.01); *A61K 33/30* (2013.01); *A61K 33/32* (2013.01); *A61K 33/34* (2013.01); *A61P 31/04* (2018.01); *A23V 2002/00* (2013.01); *A23V 2200/324* (2013.01); *A23V 2250/04* (2013.01); *A23V 2250/1588* (2013.01); *A23V 2250/1642* (2013.01); *A61K 9/145* (2013.01); *A61K 9/2018* (2013.01)

(58) Field of Classification Search
CPC ...... A23K 20/30; A23K 20/105; A23K 50/30; A61K 33/34; A61K 33/30; A61K 9/0053; A61K 9/145; A61K 2300/00; A61P 31/04; A23V 2002/00; A23V 2200/324; A23V 2250/04; A23V 2250/1642; A23V 2250/1588
See application file for complete search history.

(56) References Cited

U.S. PATENT DOCUMENTS

| | | |
|---|---|---|
| 5,405,836 A | 4/1995 | Richar et al. |
| 2005/0123623 A1* | 6/2005 | Carter .................... A61K 31/60 424/637 |
| 2007/0185216 A1 | 8/2007 | Snyder et al. |
| 2008/0166426 A1 | 7/2008 | Pekoe |
| 2013/0095184 A1* | 4/2013 | Lyczak .................. A01N 59/16 424/490 |
| 2013/0195998 A1 | 8/2013 | Tel-Ari |
| 2013/0302382 A1* | 11/2013 | DiSilvestro .......... A61K 31/685 424/400 |
| 2014/0179645 A1 | 6/2014 | Arndt |

FOREIGN PATENT DOCUMENTS

| | | |
|---|---|---|
| AU | 2013/202114 B2 | 10/2014 |
| MX | 2010/008389 A | 5/2011 |
| WO | WO 01/00021 A1 | 1/2001 |
| WO | WO 2011/069227 A1 | 6/2011 |
| WO | WO 2012/112230 A2 | 8/2012 |
| WO | WO 2013/159865 A1 | 10/2013 |

OTHER PUBLICATIONS

Gaudre et al. "What mineral and vitamin levels to recommend in swine diets?" R. Bras. Zootec., 2009, 38: 190-200. (Year: 2009).*

* cited by examiner

*Primary Examiner* — Doan T Phan
(74) *Attorney, Agent, or Firm* — Trojan Law Offices

(57) ABSTRACT

The present invention relates to the use of zinc and copper gluconate in the treatment of methicillin-resistant *Staphylococcus aureus* and dietary supplements for mammals comprising zinc and copper gluconate and their use in treatment of methicillin-resistant *Staphylococcus aureus*.

10 Claims, No Drawings

USE OF ZINC AND COPPER GLUCONATE IN THE TREATMENT OF METHICILLIN-RESISTANT *STAPHYLOCOCCUS AUREUS*

CROSS-REFERENCES TO RELATED APPLICATIONS

The present application is a U.S. National Stage Application under 35 U.S.C. 371 of PCT/DK2016/050069, filed on Mar. 11, 2016, which claims priority to Danish Patent Application PA 2015 00152, filed on Mar. 11, 2015.

FIELD

Use of zinc and copper gluconate in the treatment of methicillin-resistant *Staphylococcus aureus* in mammals is disclosed.

BACKGROUND

Zinc is a necessary component for the functioning of more than 300 different enzymes and plays a vital role in a large number of biological processes. Zinc is a cofactor for the antioxidant enzyme superoxide dismutase (SOD) and is in a number of enzymatic reactions involved in carbohydrate and protein metabolism.

Zinc has a well-recognized importance as an immune-enhancing cofactor necessary for the regulation of T lymphocytes, CD4 cells, natural killer cells, and interleukin-2. In addition, it has been claimed that zinc possesses antiviral activity. Zinc is necessary for the maturation of sperm and normal fetal development. It is involved in sensory perception (taste, smell, and vision) and controls the release of stored vitamin A from the liver. In the endocrine system, zinc has been shown to regulate insulin activity and promote the conversion of the thyroid hormone thyroxine to triiodothyronine.

Zinc, in the form of e.g. zinc sulfate, zinc gluconate or zinc acetate has been administered orally to humans in the form of pills dissolvable in the gastric system or in the form of lozenges dissolvable in the saliva of the mouth. It is known that in domesticated animals zinc gluconate e.g. baked into dog biscuits is beneficial in curing e.g. halitosis in dogs (U.S. Pat. No. 5,405,836) or added in powdery form to animal feed for improving the immune system response of domesticated animals. Danish Patent Application PA 199901119 describes the use of zinc gluconate in a dietary supplement for pigs useable in the treatment of lung disease in pigs.

Oral administration of zinc to humans in the form of tablets or pills is well recognized as a necessary dietary supplement and vitamin pills comprising zinc e.g. in the form of zinc gluconate are commonly sold in many countries of the world. A daily dose of 10 mg zinc is considered adequate as a dietary supplement.

In the farming industry, piglets which have been removed from the sow before the end of the natural suckling period are routinely fed dietary supplements comprising zinc oxides to prevent diarrhea. This praxis is known to increase the occurrence of methicillin-resistant *Staphylococcus aureus* (MRSA) in the pig pens of the farming industry.

A particular problem with the administration of zinc to mammals is the low uptake of zinc in the digestive system. E.g. only 20% of added zinc is taken up by the digestive system when administered as pills of zinc oxide. The remaining zinc is excreted in the feces.

The current inventor has therefore realized the need for an improved source of zinc and other minerals for mammalian dietary supplements which can hinder, prevent, or even treat infestations with MRSA.

SUMMARY OF THE INVENTION

In a first aspect and embodiment of the invention there is disclosed the use of zinc and copper gluconate in the treatment of methicillin-resistant *Staphylococcus aureus* in mammals.

In a second embodiment there is disclosed a use according to the first embodiment wherein said mammal belongs to the genus *Sus* of the Suidae family.

In a third embodiment there is disclosed a use according to the second embodiment wherein zinc gluconate is administered in a daily dose of between 50 to 80 mg zinc/kg feed, with 65 mg zinc/kg feed being preferred.

In a fourth embodiment there is disclosed a use according to the second embodiment wherein copper gluconate is administered in a daily dose of between 5 to 25 mg copper/kg feed, with 15 mg copper/kg feed being preferred.

In a fifth embodiment there is disclosed a use according to the second embodiment wherein zinc gluconate is administered in a daily dose of 65 mg zinc/kg feed and copper gluconate is administered in a daily dose of 15 mg copper/kg feed.

In a sixth embodiment there is disclosed a use according to the first embodiment wherein the mammal is a human.

In a seventh embodiment there is disclosed a use according to said sixth embodiment wherein zinc gluconate is administered in a daily dose of 50% of recommended daily intake.

In an eighth embodiment there is disclosed a use according to the sixth embodiment wherein copper gluconate is administered in a daily dose of 25% of recommended daily intake.

In a ninth embodiment there is disclosed a use according to the sixth embodiment wherein zinc gluconate is administered in a daily dose of 50% and copper gluconate is administered in a daily dose of 25% of recommended daily intake.

In a tenth embodiment there is disclosed a use according to any of the sixth to ninth embodiments wherein zinc gluconate and/or copper gluconate are administered as a powder.

In an eleventh embodiment there is disclosed a use according to the tenth embodiment wherein the powder is comprised in a lozenge, a bonbon or an oral disposable tablet.

In an twelfth embodiment there is disclosed a use according to any of the previous embodiments wherein zinc gluconate and/or copper gluconate are administered to a mammal in need thereof for at least 4 weeks, preferably 8 weeks.

In a thirteenth embodiment there is disclosed an animal feed supplement comprising zinc and copper gluconate for use in the treatment of methicillin-resistant *Staphylococcus aureus* in mammals according to any of the first to fifth embodiments.

In a fourteenth embodiment there is disclosed an animal feed supplement according to the thirteenth embodiment comprising zinc gluconate in a daily dose of 65 mg zinc/kg feed and copper gluconate in a daily dose of 15 mg copper/kg feed.

In a fifteenth embodiment there is disclosed a powder comprising zinc and copper gluconate for use in the treatment of methicillin-resistant *Staphylococcus aureus* in mammals according to any of the sixth to twelfth embodiments.

In a sixteenth embodiment there is disclosed a powder according to the fifteenth embodiment wherein zinc is comprised in the powder to a weight of between 1 mg and 100 mg zinc per gram powder.

In a seventeenth embodiment there is disclosed a powder according to the fifteenth embodiment comprising copper to a weight of between 0.1 mg and 1 mg copper per gram powder.

In an eighteenth embodiment there is disclosed a powder according to any of the fifteenth to seventeenth embodiments further comprising manganese to a weight of between 0.1 mg and 2 mg manganese per gram powder.

In a nineteenth embodiment there is disclosed a powder according to any of the fifteenth to eighteenth embodiments comprising zinc to a weight between 1 mg and 100 mg zinc, copper to a weight between 0.1 mg and 1 mg copper, manganese to a weight between 0.1 mg and 2 mg manganese per gram powder.

In a twentieth embodiment there is disclosed a powder according to the fifteenth embodiment wherein the powder comprises 10 mg zinc, 0.5 mg copper, and 0.8 mg manganese per gram powder.

In a twenty-first embodiment there is disclosed a powder according to the fifteenth embodiment wherein the powder comprises 75 mg zinc, 0.5 mg copper, and 0.8 mg manganese per gram powder.

In a twenty-second embodiment there is disclosed a powder according to any of the fifteenth to twenty-first embodiments further comprising a water soluble carrier substance, preferably sucrose, or dextrose, most preferably dextrose.

In a twenty-third embodiment there is disclosed a dietary supplement comprising a powder according to anyone of the fifteenth to twenty-second embodiments.

In a twenty-fourth embodiment there is disclosed a method of treatment of methicillin-resistant *Staphylococcus aureus* in mammals comprising an oral administration of zinc gluconate and copper gluconate.

In a twenty-fifth embodiment there is disclosed a method of treatment of methicillin-resistant *Staphylococcus aureus* in mammals comprising an oral administration of zinc gluconate and copper gluconate, wherein the mammals belong to the genus *Sus* of the Suidae family.

In a twenty-sixth embodiment there is disclosed a method of treatment of methicillin-resistant *Staphylococcus aureus* in mammals comprising oral administration of zinc gluconate and copper gluconate, wherein zinc gluconate is administered in a daily dose of between 50 to 80 mg zinc/kg feed with 65 mg zinc/kg feed being preferred.

In a twenty-seventh embodiment there is disclosed a method of treatment of methicillin-resistant *Staphylococcus aureus* in mammals comprising oral administration of zinc gluconate and copper gluconate, wherein copper gluconate is administered in a daily dose of between 5 to 25 mg copper/kg feed with 15 mg copper/kg feed being preferred.

In a twenty-eighth embodiment there is disclosed a method of treatment of methicillin-resistant *Staphylococcus aureus* in mammals comprising oral administration of zinc gluconate and copper gluconate wherein, individually, zinc gluconate is administered in a daily dose of between 50 to 80 mg zinc/kg feed, and copper gluconate is administered in a daily dose of between 5 to 25 mg copper/kg feed, the combination 65 mg zinc/kg feed and 15 mg copper/kg feed being preferred.

In a twenty-ninths embodiment there is disclosed a method of treatment of methicillin-resistant *Staphylococcus aureus* in mammals comprising oral administration of zinc gluconate and copper gluconate, wherein mammal is a human.

In a thirtieth embodiment there is disclosed a method of treatment of methicillin-resistant *Staphylococcus aureus*, wherein zinc gluconate is administered in a daily dose of 50% of recommended daily intake.

In a thirty-first embodiment there is disclosed a method of treatment of methicillin-resistant *Staphylococcus aureus*, wherein copper gluconate is administered in a daily dose of 25% of recommended daily intake.

In a thirty-second embodiment there is disclosed a method of treatment of methicillin-resistant *Staphylococcus aureus*, wherein zinc gluconate is administered in a daily dose of 50% and copper gluconate is administered in a daily dose of 25% of recommended daily intake.

In a thirty-second embodiment there is disclosed a method of treatment of methicillin-resistant *Staphylococcus aureus*, wherein zinc gluconate and/or copper gluconate are administered as a powder.

In a thirty-third embodiment there is disclosed a method of treatment of methicillin-resistant *Staphylococcus aureus*, wherein powder is comprised in a lozenge, a bonbon or an oral disposable tablet.

In a thirty-fourth embodiment there is disclosed a method of treatment of methicillin-resistant *Staphylococcus aureus*, wherein zinc gluconate and/or copper gluconate are administered to a mammal in need thereof for at least 4 weeks, preferably 8 weeks.

In a thirty-fifth embodiment there is disclosed a method of treatment of methicillin-resistant *Staphylococcus aureus*, wherein zinc gluconate and copper gluconate are administered as an animal feed supplement.

In a thirty-sixth embodiment there is disclosed a method of treatment of methicillin-resistant *Staphylococcus aureus*, wherein zinc gluconate and copper gluconate are administered as a dietary supplement.

In a thirty-seventh embodiment there is disclosed a use of zinc gluconate and copper gluconate for the manufacture of a medicament for the oral treatment of methicillin-resistant *Staphylococcus aureus* in mammals.

In a thirty-eighths embodiment there is disclosed a use of zinc gluconate and copper gluconate for the manufacture of a medicament for the oral treatment of methicillin-resistant *Staphylococcus aureus*, wherein a mammal belongs to the genus *Sus* of the Suidae family.

In a thirty-ninths embodiment there is disclosed a use of zinc gluconate and copper gluconate for the manufacture of a medicament for the oral treatment of methicillin-resistant *Staphylococcus aureus*, wherein the mammal is a human.

In a fortieth embodiment there is disclosed a use of zinc gluconate and copper gluconate for the manufacture of a medicament for the oral treatment of methicillin-resistant *Staphylococcus aureus*, wherein the medicament is a powder.

In a forty-first embodiment there is disclosed a use of zinc gluconate and copper gluconate for the manufacture of a medicament for the oral treatment of methicillin-resistant *Staphylococcus aureus*, wherein the powder is comprised in a lozenge, a bonbon or an oral disposable tablet.

In a forty-second embodiment there is disclosed a use of zinc gluconate and copper gluconate for the manufacture of a medicament for the oral treatment of methicillin-resistant *Staphylococcus aureus*, the powder comprising zinc to a weight of between 1 mg and 100 mg zinc per gram powder.

In a forty-third embodiment there is disclosed a use of zinc gluconate and copper gluconate for the manufacture of a medicament for the oral treatment of methicillin-resistant *Staphylococcus aureus*, the medicament comprising, the powder comprising copper to a weight of between 0.1 mg and 1 mg copper per gram powder.

In a forty-forth embodiment there is disclosed a use of zinc gluconate and copper gluconate for the manufacture of a medicament for the oral treatment of methicillin-resistant *Staphylococcus aureus*, the powder further comprising manganese to a weight of between 0.1 mg to 2 mg manganese per gram powder.

In a forty-fifth embodiment there is disclosed a use of zinc gluconate and copper gluconate for the manufacture of a medicament for the oral treatment of methicillin-resistant *Staphylococcus aureus*, the powder comprising zinc to a weight between 1 mg and 100 mg zinc, copper to a weight between 0.1 mg and 1 mg copper, manganese to a weight between 0.1 mg and 2 mg manganese per gram powder.

In a forty-sixth embodiment there is disclosed a use of zinc gluconate and copper gluconate for the manufacture of a medicament for the oral treatment of methicillin-resistant *Staphylococcus aureus*, the powder comprising 10 mg zinc, 0.5 mg copper, and 0.8 mg manganese per gram powder.

In a forty-seventh embodiment there is disclosed a use of zinc gluconate and copper gluconate for the manufacture of a medicament for the oral treatment of methicillin-resistant *Staphylococcus aureus*, the powder comprising 75 mg zinc, 0.5 mg copper, and 0.8 mg manganese per gram powder.

In a forty-eighths embodiment there is disclosed a use of zinc gluconate and copper gluconate for the manufacture of a medicament for the oral treatment of methicillin-resistant *Staphylococcus aureus* 8, the powder further comprising a water soluble carrier substance, preferably sucrose, or dextrose, most preferably dextrose.

In a forty-ninths embodiment there is disclosed a use of zinc gluconate and copper gluconate for the manufacture of a medicament for the oral treatment of methicillin-resistant *Staphylococcus aureus*, wherein the powder is an animal feed supplement.

In a fiftieth embodiment there is disclosed a use of zinc gluconate and copper gluconate for the manufacture of a medicament for the oral treatment of methicillin-resistant *Staphylococcus aureus*, wherein the powder is an animal feed supplement.

In a fiftieth embodiment there is disclosed a use of zinc gluconate and copper gluconate for the manufacture of a medicament for the oral treatment of methicillin-resistant *Staphylococcus aureus*, wherein the powder is a dietary supplement.

DETAILED DESCRIPTION

The present invention relates to the prevention and treatment of infestations with methicillin-resistant *Staphylococcus aureus* (MRSA) in mammals by intake of zinc and copper gluconate, preferably by intake in the food or as powders.

In the tests performed by the inventor it has been discovered that the method of the present invention is well suited as a dietary supplement for mammals and in particular suitable as a dietary supplement for humans as well as mammals of the genus *Sus* of the Suidae family, in particular in domesticated pigs.

In a first aspect and embodiment of the invention there is disclosed the use of zinc and copper gluconate in the treatment of methicillin-resistant *Staphylococcus aureus* in mammals.

When the mammal belongs to the genus *Sus* of the Suidae family, common pig, zinc gluconate can be administered in a daily dose of between 50 to 80 mg zinc/kg feed, preferably between 55 to 75 mg zinc/kg feed, more preferably between 60 to 70 mg zinc/kg feed, and most preferably 65 mg zinc/kg feed.

When the mammal belongs to the genus *Sus* of the Suidae family, common pig, copper gluconate can be administered in a daily dose of between 5 to 25 mg copper/kg feed, preferably between 10 to 20 mg copper/kg feed, more preferably between 12.5 to 17.5 mg copper/kg feed, and most preferably 15 mg copper/kg feed.

When the mammal belongs to the genus *Sus* of the Suidae family, common pig, zinc gluconate can be administered in a daily dose of between 50 to 80 mg zinc/kg feed and copper gluconate administered in a daily dose of between 5 to 25 mg copper/kg feed the amounts of zinc and copper varying independently of each other. A particularly preferred combination is 65 mg zinc/kg feed and 15 mg copper/kg feed.

When the mammal belongs to the genus *Sus* of the Suidae family, common pig, said zinc gluconate and/or said copper gluconate is administered to a mammal in need thereof for at least 4 weeks, for 5 weeks, for 6 weeks, preferably for 7 weeks and most preferably for 8 weeks.

Further there is disclosed an animal feed supplement comprising zinc and copper gluconate for use in the treatment of methicillin-resistant *Staphylococcus aureus* in mammals. When the mammal belongs to the genus *Sus* of the Suidae family, common pig, the animal feed comprises zinc gluconate in a daily dose of between 50 to 80 mg zinc/kg feed and copper gluconate in a daily dose of between 5 to 25 mg copper/kg feed.

Further, the present invention discloses a powder for use in a dietary supplement for a human, the powder comprising zinc gluconate.

Preferably, zinc comprising powder further is prepared such that it does not comprise of an amount of a compound or substance, wherein the amount of compound or substance is suitable for lowering or raising the pH of the mouth of said human below moderate acidic or above neutral. In a preferred embodiment the powder comprises a buffer substance capable of maintaining a moderately acidic to neutral pH in said human's mouth, preferably maintaining the pH of the mouth at physiological pH of 7.2-7.4.

A unit dose of the present invention has a weight between 0.2 g to 2 g, between 0.5 g to 1.5 g, between 0.8 g to 1.2 g. Preferably a unit dose of the present invention has a weight of 1 g.

Preferably, zinc is comprised in the unit dose to a weight of between 100 mg and 1 mg zinc, 75 mg and 2 mg zinc, 50 mg and 5 mg zinc, 25 mg and 7 mg zinc, or 10 mg zinc.

In one embodiment zinc is comprised in the unit dose to a weight of 10 mg zinc; this embodiment being particularly useful as a long term dietary supplement wherein the recommended daily supplementary dietary amount of zinc is given with the unit dose.

In another embodiment zinc is comprised in the unit dose to a weight of between 100 mg and 50 mg zinc, preferably 75 mg zinc.

To avoid problems with zinc-induced copper deficiency and/or manganese deficiency it is suggested to include in further embodiments of the present invention additional constituent minerals of the powder in the form of water soluble copper and/or water soluble manganese compounds.

The powder of the present invention therefore comprises copper gluconate.

Preferably copper is comprised in the unit dose to a weight of between 1 mg and 0.1 mg copper, 0.8 mg and 0.2 mg copper, 0.6 mg and 0.3 mg copper, 0.5 mg and 0.4 mg copper, preferably 0.5 mg copper.

The powder of the present invention therefore further optionally comprises a water soluble manganese compound, said manganese compound preferably being manganese gluconate.

Preferably, manganese is comprised in the unit dose to a weight of between 2 mg and 0.1 mg manganese, 1.5 mg and 0.3 mg manganese, 1.2 mg and 0.5 mg manganese, 1 mg and 0.6 mg manganese, preferably 0.8 mg manganese.

The powder of the present invention optionally comprises a buffer substance capable of maintaining a stable pH in the pH-interval from pH 5 to pH 8.5, preferably maintaining a stable pH at physiological conditions of the mouth at pH 7.2 to 7.4. E.g. a Hepes buffer or a sodium phosphate buffer in powdery form could fulfill these requirements.

The powder of the present invention further comprises a water soluble carrier substance, the carrier substance being able to form a powder dissolvable in saliva; preferably the carrier substance being easily dissolvable in saliva. Preferably, the water soluble carrier substance is a monosaccharide or a disaccharide, most preferably the carrier substance is sucrose or dextrose, most preferably dextrose. Experiments have shown that when dextrose is used as the water soluble carrier substance, it is rapidly and completely dissolved in the mouth while not hindering the uptake of the minerals comprised in said powder.

Preferably the water soluble carrier substance is present in the unit dose to a weight between 0.2 g to 2 g, between 0.5 g to 1.5 g, between 0.8 g to 1.2 g, preferably between 0.9 g to 1.1 g.

To prepare a unit dose of the powder having a predetermined weight such as e.g. 1 g, a weight of the water soluble zinc compound, and, optionally, a weight of the water soluble copper compound, and/or, optionally, a weight of the water soluble manganese compound, is mixed and added to a weight of the water soluble carrier substance to obtain the unit dose having the predetermined weight. When the optional buffer substance is present, the weight of the water soluble carrier substance is adjusted accordingly.

A powder of the present invention comprises zinc to a weight between 1 mg and 100 mg zinc, and copper to a weight between 0.1 mg and 1 mg copper, and optionally manganese to a weight between 0.1 mg and 2 mg manganese to 1 g of powder.

A particular powder of the present invention comprises zinc to a weight between 1 mg and 100 mg zinc, copper to a weight between 0.1 mg and 1 mg copper, manganese to a weight between 0.1 mg and 2 mg manganese to 1 g of powder.

One particularly useful mixture of the above mentioned compounds is obtained when the powder comprises 10 mg zinc, 0.5 mg copper, and 0.8 mg manganese to 1 g of powder.

A further particularly useful mixture of the above mentioned compounds is obtained when the powder comprises 75 mg zinc, 0.5 mg copper, and 0.8 mg manganese to 1 g of powder.

In a particularly preferred embodiment of the unit dose, zinc is present in the form of zinc gluconate, copper is present in the form of copper gluconate and manganese is present in the form of manganese gluconate with the balance made up by the water soluble carrier substance in the form of dextrose.

A powder of this preferred embodiment is made by preparing a first compound mixture by mixing zinc gluconate, copper gluconate and manganese gluconate to a desired ratio by weight of these compounds and then mixing the first compound mixture with the water soluble carrier substance and the optional buffer substance to obtain a powder having the desired concentrations of the constituent minerals. The skilled person will know to make adequate modifications of this procedure to compensate for variations in the concentrations of the constituents depending on the desired powder characteristics.

As an example, one particularly useful mixture of the above mentioned compounds is obtained when the powder comprises 10 mg zinc, 0.5 mg copper, and 0.8 mg manganese to 1 g of powder. Therein zinc gluconate, copper gluconate and manganese gluconate are mixed to a ratio of 88:3.5:8.5 by weight and then this first compound mixture is mixed with dextrose to a ratio of 8:92 by weight.

Powders of the present invention are characterized by their cut-off size. There is an advantage to using powders having cut-off sizes which in the context of the present application can be considered as small rather than large in that the dissolution in the mouth is more rapid when smaller powder particles are used due to the increased surface to volume ratio of such particles. However, the efficacy of the disclosed powders is not affected by the cut-off size of these powders only the time to achieve dissolution of the powder.

In the context of the present invention, powders having a specified cut-off size are prepared in the following manner. A powder is sieved through a filter having a predetermined filter size, said predetermined filter size defining said cut-off size. Only powder particles having an average particle size smaller than the cut-off size will pass the filter having said predetermined filter size. All powder particles having passed said filter will then confirm to the criteria of having an average powder particle size smaller than said cut-off size. A second filter (or further) filters having a second (or further) and smaller cut-off size can be applied additionally to characterize said powder in terms of an apparent powder size distribution.

Using this method a powder having a predetermined cut-off size can then easily be prepared from an initial batch production of powder material by sieving the initial batch powder and claiming only the material having passed through the filter for further use. The powder which did not pass the filter can be returned to the batch for further particle size reduction thereby maintaining production efficiency.

In the context of the present invention, powder particles capable of passing a filter having a cut-off size of 250 μm are considered small. Preferably, the cut-off size is smaller than 200 μm, smaller than 175 μm, preferably smaller than 150 μm, more preferably smaller than 125 μm, most preferably smaller than 100 μm. In the experiments reported in the present application all powders used were able to pass a filter having a cut-off size of approximately 150 μm corresponding to a Tyler 100 filter.

Powders of the present invention are orally administered usually as powders but adaptations of this method are possible.

In daily use it is useful to package such powders in sealable bags or containers, preferable re-sealable bags or containers. Preferably, such bags are made from plastic coated paper and such containers are made from plastics, preferably blow-molded or injection molded plastic.

When the powders of the present invention are distributed to a recipient or a patient, it is preferable that a package containing the powders of the invention further comprises a dosing unit, e.g. in the form of a dosing spoon or a dosing cup, the dosing unit capable of containing a volume of the powder, the volume corresponding to a unit dose by weight. Thereby daily use of the powders of the invention is improved for the recipient or patient.

For some recipients or patients it may not be perceived as pleasant to consume the powders of the present invention directly as powders. In such cases the powders of the invention can be administered in an oral dispersible tablet, a bonbon, or a lozenge, preferably a bonbon or a lozenge with a hard shell dissolvable in the saliva of the mouth, the powder comprised within the bonbon or lozenge. It is within the capabilities of the skilled person to make bonbons or lozenges comprising a powdery substance.

It has been found that the powders of the present invention are effective for the prevention of, or the treatment of, a number of physiological conditions and diseases caused by zinc deficiency in mammals, in particular in a human or in a mammal of the genus *Sus* of the Suidae family, in particular in a domesticated pig; when administered to said mammal, in particular to the human or the mammal of the genus *Sus* of the Suidae family, in particular to a domesticated pig; according to the improved method of administration disclosed herein.

Accordingly, in an embodiment, the present invention relates to uses of a powder comprising zinc according to the above disclosure for use in the improved method of administration disclosed herein for preventing, alleviating, or treating zinc deficiency in a mammal, in particular in a human or in a mammal of the genus *Sus* of the Suidae family, in particular in a domesticated pig.

Further in an embodiment, the present invention relates to uses of a powder comprising zinc according to the above disclosure for use in the improved method of administration disclosed herein for preventing, alleviating, or treating the common cold in a mammal, in particular in a human or in a mammal of the genus *Sus* of the Suidae family, in particular in a domesticated pig.

Further in an embodiment, the present invention relates to uses of a powder comprising zinc according to the above disclosure for use in the improved method of administration disclosed herein for preventing, alleviating, or treating pneumonia in a human.

Further in an embodiment, the present invention relates to uses of a powder comprising zinc according to the above disclosure for use in the improved method of administering disclosed herein for preventing, alleviating, or treating an infection with *salmonella* in a mammal, in particular in a human or in a mammal of the genus *Sus* of the Suidae family, in particular in a domesticated pig.

Further in an embodiment, the present invention relates to uses of a powder comprising zinc according to the above disclosure for use in the improved method of administration disclosed herein for preventing, alleviating, or treating disorders of the skin in a mammal, in particular in a human or in a mammal of the genus *Sus* of the Suidae family, in particular in a domesticated pig.

Preferably, with disorders of the skin is meant skin cancer, psoriasis, skin lesions, wounds, blisters in the mouth, or acne, preferably psoriasis, skin lesions, wounds or blisters in the mouth, most preferably wounds or blisters in the mouth.

Further in an embodiment, the present invention relates to uses of a powder comprising zinc according to the above disclosure for use in the improved method of administration disclosed herein for preventing, alleviating, or treating halitosis in a mammal, in particular in a human or in a mammal of the genus *Sus* of the Suidae family, in particular in a domesticated pig.

Further in an embodiment, the present invention relates to uses of a powder comprising zinc according to the above disclosure for use in the improved method of administration disclosed herein for preventing, alleviating, or treating necrosis of nails in a mammal, in particular in a human or in a mammal of the genus *Sus* of the Suidae family, in particular in a domesticated pig.

Further provided herein are methods of treatment of methicillin-resistant *Staphylococcus aureus* in mammals comprising oral administration of zinc gluconate and copper gluconate.

Further provided herein is the use of zinc gluconate and copper gluconate for the manufacture of a medicament for the oral treatment of methicillin-resistant *Staphylococcus aureus* in mammals.

The method of the invention is in particular beneficial for preventing, alleviating, or treating pneumonia in a human; for preventing, alleviating, or treating an infection with *salmonella* in a mammal, in particular in a human or in a mammal of the genus *Sus* of the Suidae family, in particular in a domesticated pig; for preventing, alleviating, or treating disorders of the skin in a mammal, in particular in a human or in a mammal of the genus *Sus* of the Suidae family, in particular in a domesticated pig. Preferably, with disorders of the skin is meant skin cancer, psoriasis, skin lesions, wounds, blisters in the mouth, or acne, preferably psoriasis, skin lesions, wounds or blisters in the mouth, most preferably wounds or blisters in the mouth; for preventing, alleviating, or treating halitosis in a mammal, in particular in a human or in a mammal of the genus *Sus* of the Suidae family, in particular in a domesticated pig; for preventing, alleviating, or treating necrosis of nails in a mammal, in particular in a human or in a mammal of the genus *Sus* of the Suidae family, in particular in a domesticated pig.

Oral administration includes but not limited to tablets to swallow, chew or dissolve in water or under the tongue; capsules and chewable capsules; time-release or sustained-release capsules, powder or granules, teas, drops, liquid solutions or syrups. Powders and liquid medications are most preferred for the use in the method.

In some embodiments of methods and uses mammals belongs to the genus *Sus* of the Suidae family, i.e domesticated pigs.

In some embodiments of methods and uses the doses are calculated per kg of feed. The daily dose of animal feed is known to a person skilled in the art and, therefore, is not limiting for the invention.

In some embodiments of methods and uses zinc gluconate is administered in a dose of between 50 to 80 mg zinc/kg feed, preferably with 55 mg zinc/kg feed, preferably with 60 mg zinc/kg feed, preferably with 70 mg zinc/kg feed, preferably with 75 mg zinc/kg feed, most preferably with 65 mg zinc/kg feed.

In some embodiments of methods and uses copper gluconate is administered in a daily dose of between 5 to 25 mg copper/kg feed, preferably in a dose 10 mg copper/kg feed, preferably in a dose 20 mg copper/kg feed, most preferably in a dose 15 mg copper/kg feed.

In some embodiments of methods and uses zinc gluconate is administered in a daily dose of between 50 to 80 mg zinc/kg feed and copper gluconate is administered in a daily dose of between 5 to 25 mg copper/kg feed, preferably zinc gluconate is administered in a daily dose of between 50 to 60 mg zinc/kg feed and copper gluconate is administered in a daily dose of between 5 to 10 mg copper/kg feed, preferably zinc gluconate is administered in a daily dose of between 60 to 70 mg zinc/kg feed and copper gluconate is administered in a daily dose of between 5 to 10 mg copper/kg feed, preferably zinc gluconate is administered in a daily dose of between 70 to 80 mg zinc/kg feed and copper gluconate is administered in a daily dose of between 5 to 10 mg copper/kg feed, preferably zinc gluconate is administered in a daily dose of between 50 to 60 mg zinc/kg feed and said copper gluconate is administered in a daily dose of between 10 to 15 mg copper/kg feed; preferably zinc gluconate is administered in a daily dose of between 60 to 70 mg zinc/kg feed and copper gluconate is administered in a daily dose of between 10 to 15 mg copper/kg feed; preferably zinc gluconate is administered in a daily dose of between 60 to 70 mg zinc/kg feed and copper gluconate is administered in a daily dose of between 10 to 15 mg copper/kg feed; preferably zinc gluconate is administered in a daily dose of between 70 to 80 mg zinc/kg feed and copper gluconate is administered in a daily dose of between 10 to 15 mg copper/kg feed; preferably zinc gluconate is administered in a daily dose of between 50 to 60 mg zinc/kg feed and copper gluconate is administered in a daily dose of between 15 to 20 mg copper/kg feed; preferably zinc gluconate is administered in a daily dose of between 60 to 70 mg zinc/kg feed and copper gluconate is administered in a daily dose of between 15 to 20 mg copper/kg feed; preferably zinc gluconate is administered in a daily dose of between 70 to 80 mg zinc/kg feed and copper gluconate is administered in a daily dose of between 15 to 20 mg copper/kg feed; preferably zinc gluconate is administered in a daily dose of between 50 to 60 mg zinc/kg feed and copper gluconate is administered in a daily dose of between 20 to 25 mg copper/kg feed; zinc gluconate is administered in a daily dose of between 60 to 70 mg zinc/kg feed and copper gluconate is administered in a daily dose of between 20 to 25 mg copper/kg feed; zinc gluconate is administered in a daily dose of between 70 to 80 mg zinc/kg feed and copper gluconate is administered in a daily dose of between 20 to 25 mg copper/kg feed; most preferably in the combination 65 mg zinc/kg feed and 15 mg copper/kg feed.

In some embodiments of methods and uses the mammal is a human.

In some embodiments of methods and uses zinc gluconate is administered in a daily dose of 50% of recommended daily intake.

In some embodiments of methods and uses copper gluconate is administered in a daily dose of 25% of recommended daily intake.

In some embodiments of methods and uses zinc gluconate is administered in a daily dose of 50% and copper gluconate is administered in a daily dose of 25% of recommended daily intake.

In some embodiments of methods and uses zinc gluconate and/or copper gluconate are administered as a powder.

In some embodiments of methods and uses powder is comprised in a lozenge, a bonbon or an oral disposable tablet.

In some embodiments of methods and uses zinc gluconate and/or copper gluconate are administered to a mammal in need thereof for at least 4 weeks, preferably 5 weeks, preferably 6 weeks, preferably 7 weeks, most preferably 8 weeks.

In some embodiments of methods and uses zinc gluconate and copper gluconate are administered as an animal feed supplement.

In some embodiments of methods and uses zinc gluconate and copper gluconate are administered as a dietary supplement.

In some embodiments of methods and uses the medicament comprises zinc to a weight of between 1 mg and 100 mg zinc per gram powder, preferably between 1 mg and 90 mg zinc per gram powder, preferably between 1 mg and 80 mg zinc per gram powder, preferably between 1 mg and 70 mg zinc per gram powder, preferably between 1 mg and 60 mg zinc per gram powder, preferably between 1 mg and 50 mg zinc per gram powder, preferably between 1 mg and 40 mg zinc per gram powder, preferably between 1 mg and 30 mg zinc per gram powder, preferably between 1 mg and 20 mg zinc per gram powder, most preferably 10 mg zinc per gram powder.

In some embodiments of methods and uses the medicament for the oral treatment of methicillin-resistant *Staphylococcus aureus* is comprising copper to a weight of between 0.1 mg and 1 mg copper per gram powder, preferably between 0.2 mg and 0.9 mg copper per gram powder, preferably between 0.3 mg and 0.8 mg copper per gram powder, preferably between 0.4 mg and 0.7 mg copper per gram powder, most preferably 0.5 mg copper per gram powder.

In some embodiments of methods and uses the powder further comprises manganese to a weight of between 0.1 mg to 2 mg manganese per gram powder, preferably between 0.2 mg to 1.9 mg manganese per gram powder, preferably between 0.3 mg to 1.8 mg manganese per gram powder, preferably between 0.4 mg to 1.7 mg manganese per gram powder, preferably between 0.4 mg to 1.6 mg manganese per gram powder, preferably between 0.5 mg to 1.5 mg manganese per gram powder, preferably between 0.6 mg to 1.4 mg manganese per gram powder, preferably between 0.7 mg to 1.3 mg manganese per gram powder, preferably between 0.8 mg to 1.2 mg manganese per gram powder, most preferably 0.8 mg manganese per gram powder.

In some embodiments of methods and uses the powder comprises zinc to a weight between 1 mg and 100 mg zinc, copper to a weight between 0.1 mg and 1 mg copper, manganese to a weight between 0.1 mg and 2 mg manganese per gram powder.

In some embodiments of methods and uses the powder comprises 10 mg zinc, 0.5 mg copper, and 0.8 mg manganese per gram powder.

In some embodiments of methods and uses the powder comprises 75 mg zinc, 0.5 mg copper, and 0.8 mg manganese per gram powder.

In some embodiments of methods and uses the powder further comprises a water soluble carrier substance, preferably sucrose, or dextrose, most preferably dextrose.

In some embodiments of methods and uses the powder is an animal feed supplement.

In some embodiments of methods and uses the powder is a dietary supplement.

EXAMPLES

Prior Art

The safety and efficacy of zinc gluconate as a powder and used as a conventional dietary supplement is well recognized in the literature.

Test of Efficacy and Safety

In a confirmation experiment the safety of using powdered zinc gluconate as a conventional dietary supplement in the dietary mineral supply of domesticated pigs was examined in a controlled study. The study population was inspected regularly by a veterinarian for signs of malnourishment or increased infection levels but no signs of these conditions were observed.

3 groups of pigs, each comprising 11 individuals were identically fed save for the source of zinc as according to Table 1. Group 1, which was the control group, was fed 50 g 75% zinc oxide per ton dry feed according to normal feeding recommendations. Group 2 was fed zinc gluconate as a powder. Group 3 was fed zinc gluconate and further including 100 g Micro Aid® per ton feed. The amount of zinc fed to the animals of the three study groups was identical and corresponding to 23 g zinc per ton dry feed. Micro Aid® is dietary supplement known to enhance growth and reduce ammonia excretions in domesticated pigs. It is a registered trade mark of DPI Global, 17656 Avenue 168, Porterville, Calif. 93257. Micro Aid® has a recognized effect on the growth increase of pigs on the order of 4% per 100 g added Micro Aid® per ton feed.

The daily gain of weight for each individual was registered during the trial period and the trial was terminated after 83 days. For comparison the expected weight gain of adding Micro Aid® to a feed mixture comprising one of the two zinc sources has been calculated.

TABLE 1

| Group | Zn-source | Average daily weight gain |
| --- | --- | --- |
| 1 | zinc oxide | 822 g/daily |
| Comparison (expected) | added Micro Aid ® and zinc oxide | 857 g/daily |
| 2 | zinc gluconate | 875 g/daily |
| 3 | zinc gluconate | 910 g/daily |
| Comparison (expected) | added Micro Aid ® and zinc gluconate | 912 g/daily |

The safety and efficacy study clearly showed that in terms of average daily weight gain zinc gluconate alone was a better source of zinc than zinc oxide and also performed better than what would be expected for a study group receiving feed comprising both zinc oxide and Micro Aid®. The study further showed that the effects of adding zinc gluconate and Micro Aid® to the dry feed were additive.

Effectiveness Against Lung Disease in Pigs

Danish Patent Application PA 199901119 describes the use of zinc gluconate in a dietary supplement for pigs useable in the prevention and treatment of lung disease in pigs. The dietary supplement corresponded to the dietary supplement given to group three in the safety and efficacy study and has formed the basis of a marketed product in Denmark, manufactured by Scan Feed ApS.

In the reported patent application the inventor discloses that the use of zinc gluconate as a dietary supplement very effectively prevented the outbreak of lung disease in pigs, decreasing the incidence rate from 4318 pigs with lung scars out of 12288 delivered to meat producing facilities during the years 1994, 1995 and 1996 to 441 pig with lung scars out of 4001 delivered to meat producing facilities during the first year (1997) of feeding the pigs at the production facility with the dietary supplement of group 3. This corresponds to a decrease in incidence rate from 35.1% to 11.0%. The original feed at the production facility corresponded to the feed of group 1 with 100 g Micro Aid® per ton feed.

Results of the Present Study:

In the below studies new results on the effect of administering zinc gluconate to mammals, in particular to humans and to mammals of the genus Sus of the Suidae family, in particular domesticated pigs.

Study 1:

In a randomized trial the effect of the addition of 0.05% zinc gluconate to a standard pellet feed was tested for efficacy against salmonella, health condition of the digestive system including stomach and intestines, and productivity in pigs, and compared to an otherwise identical diet without zinc gluconate. The control group received zinc in the form of zinc oxide to the same amount as the study group.

408 pigs from a single farm were randomly partitioned into two groups of 204 pigs each and fed with either a pelleted control feed or an otherwise identical pelleted feed comprising 0.05% zinc gluconate. In order maintain comparability of control group to study group and to diminish the influence of lung disease on the mortality of the control group, both groups were twice vaccinated with Porcilis against severe lung disease. The combined disease and mortality withdrawal rate was at 1.7% for both control group and study group while about 15% of all pigs in both groups were treated for diarrhea during the study period. There was a balanced gender level in both control and study group.

All pigs were followed for 12 weeks starting with their inclusion into the trial and ending with their transport to a meat processing plant. For all pigs in the study data on the feed uptake, growth, eventual diseases suffered during the study period were collected as well as including the complete slaughter records of the meat processing plant into the study. Pigs were included into the trial upon reaching an entry weight of on the average 33 kg. The pigs were weighed at inclusion into the trial, after 6 weeks, and after 12 weeks. Pigs on the average weighed 33 kg at inclusion, 65 kg after 6 weeks, and 105 kg after 12 weeks.

The pigs were partitioned into blocks of 10-11 individuals in each pigsty, each block having comparable entry times. The pigs in the study were allowed to eat and drink freely and the access to water and dietary was unrestricted.

The study confirmed the increased feeding efficacy of pig feed comprising zinc gluconate compared to the control group. On the average a pig in the control group required 2.85 feeding units (FU) to achieve 1 kg of growth compared to 2.78 FU/kg in the study group. For pigs having weights between 33-65 kg there was no significant difference between the two groups, the groups requiring 2.53 and 2.51 FU/kg respectively, while for pigs weighing between 65-105 kg, the control group required 3.13 FU/kg while the study group only required 3.00 FU/kg.

A subset of the pigs in both study groups were tested for salmonella prior to shipping out of the test and to the meat processing facility by testing for antigens against Salmonella in the blood. An inclusion rate of 60% was desired for both groups but was not reached for the study group. The results are reported in Table 2.

TABLE 2

| Group | Control | Study |
| --- | --- | --- |
| Feed | Zinc Oxide | Zinc gluconate |
| Samples | 126 | 108 |
| Positives | 38 | 24 |
| Pct. positives | 30.2% | 22.2% |
| Relative risk | 1 | 0.56 |

The test showed a clear indication that addition of zinc gluconate to pig feed rather than zinc oxide may help to prevent a bacterial infestation in domesticated pigs, in particular an infestation with salmonella.

Both in the lung disease prevention study reported in DK-PA199901119 and the salmonella infection prevention study reported here an effect of prevention of bacterial infestation is reported. It is therefore considered credible that an improvement of the zinc-uptake in mammals will lead to an improvement in the general health situation of such mammals, in particular lead to an improvement in the general health situation of such mammals by reducing the risk of, or by preventing, bacterial infestation in such a mammal, in particular bacterial infestation by bacteria of the genus *Streptococcus* or the genus *Salmonella*.

In particular it is considered that this effect can beneficially be observed in mammals of the genus *Sus* of the Suidae family, in particular in domesticated pigs.

Study 2:

A controlled comparison study between two groups of pigs at two farms in the province of Nordjylland, Denmark, was performed, each farm having about 600 sows in production and each farm feeding the sows in the production zinc according to veterinary recommendations of 75 ppm zinc per FU. At farm 1, the sows received zinc in the form of zinc oxide whereas at farm 2, the sows received zinc in the form of zinc gluconate. A rapid decrease in the number of open wounds was observed within a month of the dietary change for the sows receiving zinc in the form of zinc gluconate, in particular in the number of sows suffering from lesions on their footpads which disappeared almost completely in the sows of farm 2.

Study 3:

In the study population of sows of farm 2 in the previous study, it was observed that these sows gave birth to piglets having an above average weight at birth and that the milk production of the sows was increased compared to the sows of farm 1.

Study 4

In a further study, the effect on infestations with methicillin-resistant *Staphylococcus aureus* of zinc and copper gluconate was examined in a test group of 50 pigs.

Farm Conditions:

Farm in the province of Nordjylland, Denmark, with 2200 pigs raised for the food processing industry, the pigs having health status SPF+Ap12. Race: Yorkshire or Yorkshire—Landrace krydsning. The pigs complement was known as infested with methicillin-resistant *Staphylococcus aureus* (MRSA). 10 nose swabs of slaughter-ready pigs were tested September 2014 of which 5 showed MRSA-positive.

Materials:

Nose swaps: Test set from Dianova, Denmark, sterile nose swaps and receptacle comprising sterile salt water.

Experimental Feed:

Standard, industrial feed for pig complements raised for slaughter with the below changes: 15 mg copper/kg feed in the form of copper sulfate replaced with an equal amount of copper in the form of copper gluconate. 65 mg zinc/kg feed in the form of zinc oxide replace with an equal amount of zinc in the form of zinc gluconate. The feed was used from first arrival of the pigs in the production unit until their removal for slaughter.

Experimental Procedure:

On the farm, a section of 200 pig units was chosen. For the duration of the experiment, no further pigs were added to the section and only pigs dead during production were removed. No pigs were exchanged between individual pigsties.

4-5 days after arrival, 50 pigs were randomly chosen (3-4 pigs in each pigsty), continuously earmarked and nose swaps performed in a random nostril and at the base of an ear on the backside. The nose swap was place 1-3 cm in the nostril and rotated for about 2 sec. before rubbing 4-6 times behind the pig's ear. The nose swap was cut to fit the receptacle with sterile salt water taking special caution not to contaminate the swap during transfer, and the receptacle numbered with the ear mark of the pig. The starting weight of the pigs at arrival was about 40 kg.

8 weeks after the first nose swap the same pigs were tested again following the above procedure. One pig could not be accounted for, probably due to a lost ear tag.

Total number of examination completions 49 of 50.

Nose Swap Evaluation:

The samples were examined for MRSA at Afdelingen for fødevaremikrobiologi, Zoonoselaboratoriet, Fødevare-instituttet, The Danish Technological University, DTU.

Results:

At the first testing at study start, 38 out of 50 examined animals were tested positive for MRSA. At the control testing after 8 weeks, four (4) pigs were found positive, all four pigs having been found positive in the first test. No pigs which had not been found positive in the first test was later tested positive.

This corresponds to a reduction by 89% of the infestation level of MRSA in pigs, solely by changing the mineral composition of the feed.

Comments:

The results were obtained over an 8 week period solely by changing the mineral composition of the feed. Antibiotics were not employed. Only such amounts of zinc and copper as would normally be added to the feed were employed.

Further Bonusses

It is a surprising realization of the present study that this beneficial effect on skin and wound healing can be enhanced by administering zinc in the form of zinc gluconate to mammals in a manner which increases the residence time of the zinc gluconate in the mouth cavity of such mammals, whereby zinc uptake is improved and an occurrence of zinc deficiency in such mammals is alleviated rapidly and consistently. In particular the effects in humans of the presented method of administration of zinc is completely unexpected and has not hitherto been described in the prior art to the knowledge of the present inventor.

Accordingly, the present invention therefore in particular discloses the use of zinc gluconate in a dietary supplement comprising zinc for the treatment of zinc deficiency in a mammal, in particular a human, in need thereof and a method of administering such a dietary supplement to a mammal, in particular to a human, for the treatment of zinc deficiency in the mammal, in particular in the human; wherein the dietary supplement is a composition comprising zinc gluconate as previously described, in particular the dietary supplement is a powder, a lozenge, a bonbon, or an oral dispersible tablet, preferably a powder or an oral dispersible tablet, most preferably a powder, and the method of administering the dietary supplement to the mammal increases the residence time of zinc gluconate in the mouth cavity of the mammal, preferably increases the residence time of zinc gluconate in the mouth cavity of the mammal such that the zinc gluconate is completely dissolved in the saliva of the mammal prior to swallowing.

Further the present invention in one embodiment discloses the use of zinc gluconate in a dietary supplement for the prevention of skin lesions caused by zinc deficiency and the treatment of skin lesions, in particular curing of wounds; wherein the dietary supplement is a composition comprising zinc gluconate as previously described, in particular the dietary supplement is a powder, a lozenge, a bonbon, or an oral dispersible tablet, preferably a powder or an oral dispersible tablet, most preferably a powder, and the method of administering the dietary supplement to the mammal increases the residence time of zinc gluconate in the mouth cavity of the mammal, preferably increases the residence time of zinc gluconate in the mouth cavity of the mammal such that the zinc gluconate is completely dissolved in the saliva of the mammal prior to swallowing.

The prior embodiment, wherein the curing of skin lesions is improved and/or accelerated by treating a zinc deficiency in a mammal, in particular a human, in need thereof.

In a further embodiment of the present invention there is disclosed the use of zinc gluconate in a dietary supplement for the treatment of skin lesions, or for the treatment of necrosis of nails caused by zinc deficiency; wherein the dietary supplement is a composition comprising zinc gluconate as previously described, in particular the dietary supplement is a powder, a lozenge, a bonbon, or an oral dispersible tablet, preferably a powder or oral dispersible tablet, most preferably a powder, and the method of administering the dietary supplement to the mammal increases the residence time of zinc gluconate in the mouth cavity of said mammal, preferably increases the residence time of zinc gluconate in the mouth cavity of the mammal such that the zinc gluconate is completely dissolved in the saliva of the mammal prior to swallowing.

In a further embodiment of the present invention there is disclosed the use of zinc gluconate in a dietary supplement for the treatment of skin lesions, or for the treatment of necrosis of nails caused by zinc deficiency; wherein the dietary supplement is a composition comprising zinc gluconate as previously described, in particular the dietary supplement is a powder, a lozenge, a bonbon, or a oradispersible tablet, preferably a powder or oradispersible tablet, most preferably a powder, and the method of administering the dietary supplement to the mammal increases the residence time of zinc gluconate in the mouth cavity of the mammal, preferably increases the residence time of zinc gluconate in the mouth cavity of the mammal such that the zinc gluconate is completely dissolved in the saliva of the mammal prior to swallowing.

In a further embodiment of the present invention there is disclosed the use of zinc gluconate in a dietary supplement for the prevention of, or the treatment of the common cold; wherein the dietary supplement is a composition comprising zinc gluconate as previously described, in particular said dietary supplement is a powder, a lozenge, a bonbon, or an oral dispersible tablet, preferably a powder or oral dispersible tablet, most preferably a powder, and the method of administering the dietary supplement to the mammal increases the residence time of zinc gluconate in the mouth cavity of the mammal, preferably increases the residence time of zinc gluconate in the mouth cavity of the mammal such that the zinc gluconate is completely dissolved in the saliva of said mammal prior to swallowing.

Closing Comments

The term "comprising" as used in the claims does not exclude other elements or steps. The term "a" or "an" as used in the claims does not exclude a plurality.

Although the present invention has been described in detail for purpose of illustration, it is understood that such detail is solely for that purpose, and variations can be made therein by those skilled in the art without departing from the scope of the invention.

The invention claimed is:

1. A method of treatment of methicillin-resistant *Staphylococcus aureus* in a mammal belonging to the genus *Sus* of the Suidae family, the method comprising oral administration to said mammal of an animal feed comprising zinc gluconate and copper gluconate, wherein said zinc gluconate is administered in a dose of between 50 to 80 mg zinc/kg feed, and said copper gluconate is administered in a dose of between 5 to 25 mg copper/kg feed.

2. A method of treatment according to claim 1, wherein said zinc gluconate and said copper gluconate are administered to said mammal in need thereof for at least 4 weeks.

3. A method of treatment according to claim 1, wherein zinc gluconate and copper gluconate are comprised in said animal feed as an animal feed supplement.

4. A method of treatment according to claim 1, wherein, said zinc gluconate is administered in a daily dose of 65 mg zinc/kg feed, and said copper gluconate is administered in a daily dose of 15 mg copper/kg feed.

5. A method of treatment according to claim 3 wherein said animal feed supplement further comprises a water-soluble carrier substance.

6. A method of treatment according to claim 1, wherein said zinc gluconate and said copper gluconate are administered to said mammal in need thereof for at least 8 weeks.

7. A method of treatment according to claim 1, wherein said zinc gluconate is administered in a daily dose of 65 mg zinc/kg feed.

8. A method of treatment according to claim 1, wherein said copper gluconate is administered in a daily dose of 15 mg copper/kg feed.

9. A method of treatment according to claim 3, wherein said animal feed supplement is a powder.

10. A method of treatment according to claim 5, wherein said water-soluble carrier substance is either sucrose or dextrose.

* * * * *